United States Patent [19]
Horn et al.

[11] Patent Number: 5,576,196
[45] Date of Patent: Nov. 19, 1996

[54] PROCESS FOR REDUCING RNA CONCENTRATION IN A MIXTURE OF BIOLOGICAL MATERIAL USING DIATOMACEOUS EARTH

[75] Inventors: Nancy Horn, San Diego; Magda Marquet, La Jolla; Jennifer Meek; Gregg Budahazi, both of San Diego, all of Calif.

[73] Assignee: VICAL Incorporated, San Diego, Calif.

[21] Appl. No.: 372,236

[22] Filed: Jan. 13, 1995

[51] Int. Cl.$^6$ .............................. C12P 19/34; C12Q 1/68; C12Q 1/70; G01N 33/53
[52] U.S. Cl. .......................... 435/91.1; 435/91.2; 435/6; 435/5; 435/7.9
[58] Field of Search .................... 435/6, 5, 7.9, 91.1, 435/91.2

[56] References Cited

U.S. PATENT DOCUMENTS

| | | | |
|---|---|---|---|
| 5,075,430 | 12/1991 | Little et al. | 536/27 |
| 5,155,018 | 10/1992 | Gillespie et al. | 435/91 |
| 5,234,809 | 8/1993 | Boom et al. | 435/91 |

FOREIGN PATENT DOCUMENTS

| | | |
|---|---|---|
| 0268946 | 6/1988 | European Pat. Off. . |
| 0389063 | 9/1990 | European Pat. Off. . |
| 0512768 | 11/1992 | European Pat. Off. . |
| 0555798 | 8/1993 | European Pat. Off. . |
| WO95/34569 | 12/1995 | WIPO . |

OTHER PUBLICATIONS

Carter, M. J., et al. (1993) An inexpensive and simple method for DNA purifications on silica particles Nucleic Acids Research 21(4):1044.

Kuninaka et al. Chemical Abstracts vol. 88, No. 25, abstract No. 188151u: Nondenatured RNA Jun. 19, 1978.

Wang, G. et al. Chemical Abstracts vol. 120, No. 25, abstract No. 321505k; Obtaining the high–quality ribonucleic acid from yeast. Jun. 20, 1994.

Kothari, R. M., et al. (1972) RNA Fractionation on Kieselguhr columns. J. Chromatography 70:341–363.

Kuninaka, A., et al. (1980) Extraction of RNA from yeast packed into column without isomerization. Agric. Biol. Chem. 44(8):1821–1827.

Agraz et al. "Adsorption desorption of recombinant hepatitis B surface antigen (R–HBs–Ag) from P. Pastoris on a Diatomaceous Earth Matrix: Optimization of Parameters for Purification" biotechnology and Bioengineering 42: 1238–1244, 1993.

Egan et al. "Separation of *Eschericia coli* Ribosomal Ribonucleic Acids by Reversed Phase Chromatography" Biochemistry 10: 1890–1894. 1971.

Boyle and Lew, "An Inexpensive Alternative to Glassmilk for DNA Purification" Trends in Genetics 11(1) p. 8, Jan., 1995.

Hersh, E. et al. (1994) Phase I study of immunotherapy of malignant melanoma by direct gene transfer. Human Gene Therapy 5:1371–1384.

Rubin, J. et al. (1994) Phase I study of immunotherapy of hepatic metastases of colorectal carcinoma by direct gene transfer. Human Gene Therapy 5:1385–1399.

Thompson, J. (1986) A review of high–performance liquid chromatography in nucleic acids research. III. isolation, purification, and analysis of supercoiled plasmid DNA. BioChromatography 1(2):68–80.

Vogelzang, N. et al. (1994) Phase I study of immunotherapy of metastatic renal cell carcinoma by direct gene transfer into metastatic lesions. Human Gene Therapy 5:1357–1370.

Product Brochure by Celite Corp., Celite filter aids for maximum clarity at lowest cost. Lompoc, CA.

*Primary Examiner*—Stephanie W. Zitomer
*Assistant Examiner*—Dianne Rees
*Attorney, Agent, or Firm*—Knobbe, Martens, Olson & Bear

[57] ABSTRACT

The invention relates to a process for reducing RNA concentration in a mixture of biological material, comprising the steps of: (a) providing a mixture of biological material having a first concentration of RNA; (b) filtering the mixture through a diatomaceous earth material to produce a filtrate having a second concentration of RNA, wherein the second concentration is less than the first concentration; and (c) collecting the filtrate having a reduced RNA concentration.

20 Claims, No Drawings

PROCESS FOR REDUCING RNA CONCENTRATION IN A MIXTURE OF BIOLOGICAL MATERIAL USING DIATOMACEOUS EARTH

FIELD OF THE INVENTION

The invention relates to a process for reducing RNA concentration in a mixture of biological material using diatomaceous earth.

BACKGROUND OF THE INVENTION

Molecular biology depends for its importance on the existence of purified recombinant DNA plasmids. E.g., Thompson, BioChromatography 1:68 (1986); *Current Protocols in Molecular Biology*, Greene Publishing Assoc. & Wiley, 1987; and Sambrook, Fritsch, and Maniatis, *Molecular Cloning, A Laboratory Manual*, Second Edition, Cold Spring Harbor Laboratory Press, 1989. (All patents and publications cited hereunder are incorporated herein by reference.) Of critical significance to the development of a practical technology was the discovery that cells could incorporate extrachromosomal genetic material. Consequently, independently-replicating extrachromosomal DNA, such as plasmid DNA, can be used as a vehicle for the insertion into and amplification of any given DNA segment, from a wide variety of biological sources, in a suitable cell host which will maintain this genetic material.

Advances have been made in the fermentation and tissue culture processes used for both analytical and preparative scale growth of prokaryotic and eukaryotic cells recombinant plasmid DNA. These biological processes of synthesis generate the plasmid DNA product together with a complex mixture of cellular components including lipids, carbohydrates, lipoproteins, proteins, polysaccharides, chromosomal DNA, ribosomes, RNA and other macromolecular components. It is necessary to isolate plasmid DNA in a pure form for subsequent application.

Numerous procedures have been developed independently for the purification of cellular plasmid DNA. However, all of these processes share three basic features: (1) cellular growth; (2) cellular lysis; and (3) separation of plasmid DNA from cellular RNA and DNA. Various extractions are of key importance for the accurate, reproducible purification of plasmid DNA. These extractions are employed to remove the bulk of contaminating molecules (e.g., proteins, cellular DNA, RNA, etc.), especially when applied to complex biological systems. Proper extractions are essential for both chromatography and non-chromatography processes of plasmid purification.

A step-by-step conventional protocol for purification of plasmid DNA from 1 liter (1–2 g wet weight) of *E. coli* cells is presented in Table 1.

TABLE 1

PURIFICATION OF PLASMID DNA FROM 1 LITER (1–2 G) OF *E. COLI* CELLS

CELL LYSIS:

1. Resuspend cells in a final volume of 7.0 ml with Buffer A. Buffer A is 25 mM Tris-HCl (pH 8.0), 50 mM $Na_2EDTA$, 1% (w/v) glucose.
2. Add 14.0 ml of Buffer B; gently mix by inversion; incubate 10 min on ice. Buffer B is 0.2N NaOH, 1% SDS.
3. Add 10.5 ml of cold (4° C.) Buffer C; gently mix by inversion until white precipitate forms; incubate 5 min on ice. Buffer C is 3.0M potassium acetate, 2.0M acetic acid (pH 4.8).
4. Centrifuge 25K× g, 20 min; transfer supernatant to new tube.
5. Add exactly 2 volumes cold (–20° C.) 95% ethanol; vortex, incubate 20 min on ice.
6. Centrifuge 12K× g, 20 min; discard supernatant.

NUCLEIC ACID EXTRACTION:

7. Resuspend pellet in 1.2 ml Buffer D. Buffer D is 20 mM Tris-HCl (pH 7.2), 1 mM $Na_2EDTA$.
8. Add 0.6 ml Buffer E; vortex; incubate 20 min on ice (or 16 h, 4° C.). Buffer E is 7.5M ammonium acetate.
9. Centrifuge 12K× g, 20 min; save supernatant by transferring to new tube; discard pellet.
10. Add 4.0 ml cold (–20° C.) 95% ethanol to supernatant; vortex; incubate 20 min on ice.
11. Centrifuge 12K× g, 20 min; discard supernatant; air dry pellet (inverted) 5 min.
12. Resuspend pellet in 0.4 ml Buffer F. Buffer F is 20 mM Tris-HCl (pH 7.2), 1 mM $Na_2EDTA$, 50 mM NaCl.
13. Add 1000 units RNase; incubate 30 min at 37° C.
14. Add 0.4 ml phenol (saturated with Buffer F); vortex well.
15. Centrifuge 12K× g, 10 min; transfer upper aqueous layer to new tube.
16. Add 0.1 ml 2.0M NaCl; vortex.
17. Add 1.0 ml cold (–20° C.) 95% ethanol; vortex well, incubate 30 min (or 16 h) at –20° C.
18. Centrifuge 12K× g, 20 min; discard supernatant; wash pellet carefully with cold (–20° C.) 80% ethanol; air dry pellet (inverted) 5 min.
19. Resuspend pellet in 1.6 ml $H_2O$.

The general features of this conventional procedure are gentle treatment of the cells at pH 12.5 (step 2) to lyse the bacteria, denature chromosomal DNA, and leave the covalently closed circular plasmid DNA intact. Upon neutralization in the presence of high salt and SDS, chromosomal DNA, protein and cellular debris precipitate and are removed by centrifugation (steps 3, 4). Nucleic acids (RNA, plasmid DNA) remaining in the soluble fraction are recovered by short ethanol precipitations to reduce precipitation of any protein or chromosomal DNA contaminants (steps 5, 6). The recovered nucleic acids are incubated with 2.5M ammonium acetate to precipitate high molecular weight RNA, proteins and lipopolysaccharides which are removed by centrifugation (steps 7–9). The enriched plasmid DNA preparation is concentrated by ethanol precipitation, treated with RNase to digest RNA, phenol extracted to remove RNase and any remaining proteins and recovered by ethanol precipitation. Based on absorbance at 260 nm and subsequent purification strategies, this final sample contains about 50% plasmid DNA, 50% small RNA oligonucleotides and usually less than 1% chromosomal DNA.

Procedures such as these may be unsuitable for the manufacture of pharmaceutical-grade DNA, e.g., for the purpose of gene therapy. In this regard, there is a need for a process that reproducibly reduces host-derived RNA, which accounts for the majority of the nucleic acid in a crude lysate; that does not rely upon the use of extraneous animal-derived enzymes, such as RNases, which are susceptible of being contaminated with infectious agents; that does not depend upon the use of toxic organic extractants, such as phenol, to rid the preparation of RNases; and that uses only reagents generally recognized as safe by drug regulating bodies, such as the Food and Drug Administration (FDA).

SUMMARY OF THE INVENTION

The invention provides a process for reducing RNA concentration in a mixture of biological material, comprising the steps of: (a) providing a mixture of biological material having a first concentration of RNA; (b) filtering the mixture through a diatomaceous earth material to produce a filtrate having a second concentration of RNA, wherein the second concentration is less than the first concentration; and (c) collecting the filtrate having a reduced RNA concentration.

According to the invention, the RNA concentration may be reduced by at least about 10%, or advantageously by at least about 25%, or favorably by at least about 50% or preferably by at least about 85%.

Also, according to the invention, the mixture of biological material may be a cell lysate.

In one embodiment, the diatomaceous earth material is composed of about 90% $SiO_2$. It may be calcined. It may be flux calcined (as opposed to straight calcined). It may be acid washed (to analytical grade quality).

In another embodiment, the diatomaceous earth material has a dry density of about 10 lbs/cu.ft. It may possess a median particle size of about 22.3 microns. It may possess a median cake pore size of about 7 microns.

In a preferred embodiment, the diatomaceous earth material is composed of about 89.6% $SiO_2$, about 4.0% $Al_2O_2$, about 1.5% $Fe_2O_3$, about 0.2% $P_2O_5$, about 0.2% $TiO_2$, about 0.5% CaO, about 0.6% MgO, and about 3.3% $Na_2O+K_2O$.

In another aspect, the invention provides a process for reducing RNA concentration in a mixture of biological material, comprising the steps of: (a) providing a mixture of biological material having a first concentration of RNA; (b) exposing the mixture to a diatomaceous earth material to produce a product which, following separation from the diatomaceous earth material by filtration, centrifugation or sedimentation, has a second concentration of RNA, wherein the second concentration is less than the first; and (c) collecting the product having a reduced RNA concentration.

In still another aspect, the invention provides a process for purifying recombinant plasmid DNA from a RNA component in a mixture of biological material, comprising the steps of: (a) providing a mixture of biological material comprising recombinant plasmid DNA and having a first concentration of RNA; (b) filtering the mixture through a diatomaceous earth material to produce a filtrate comprising the recombinant plasmid DNA and having a second concentration of RNA, wherein the second concentration is less than the first concentration; and (c) collecting the filtrate having a reduced RNA component.

The recombinant plasmid DNA may be a nucleic acid-based pharmaceutical.

In yet another aspect, the invention provides a process for separating different forms of soluble RNA in a mixture of biological material, comprising the steps of: (a) providing a mixture of biological material having a first and a second form of soluble RNA; (b) filtering the mixture through a diatomaceous earth material to produce a filtrate comprising the first form of soluble RNA and a product comprising the second form of soluble RNA that collects in the diatomaceous earth material; and (c) collecting the filtrate, or eluting the second form of RNA from the diatomaceous earth material.

One of the forms of RNA may be a nucleic acid-based pharmaceutical.

In another aspect, the invention provides a process for purifying recombinant plasmid DNA from a RNA component in a mixture of biological material, comprising the steps of: (a) providing a mixture of biological material comprising recombinant plasmid DNA and having a first concentration of RNA; (b) adding a diatomaceous earth material to the mixture; (c) mixing the result of step (b) to form a suspension; (d) pouring the suspension through a diatomaceous earth precoated filter membrane to allow a diatomaceous earth cake to collect on the filter membrane and to form a filtrate comprising the recombinant plasmid DNA and having a second concentration of RNA, wherein the second concentration is less than the first concentration; and (e) collecting the filtrate having a reduced RNA component.

DETAILED DESCRIPTION OF THE INVENTION

We have discovered a process for reducing RNA concentration in a mixture of biological material using a diatomaceous earth material. While not being bound or limited by theory, it is believed that the diatomaceous earth material adsorbs RNA. Accordingly, one provides a mixture of biological material having a first concentration of RNA. One then filters the mixture through a diatomaceous earth material to produce a filtrate having a second concentration of RNA, where the second concentration is less than the first concentration. Finally, one collects the filtrate having a reduced RNA concentration.

Based on semi-quantitative analyses discussed infra, we calculate that in any one step the RNA concentration can be reduced by at least about 10%, or advantageously by at least about 25%, or favorably by at least about 50%, or preferably by at least about 85%.

Any diatomaceous earth material is contemplated. E.g., CELITE® diatomaceous earth material, as described in Product Brochure by Celite Corp., Lompoc, Calif., incorporated herein by reference. Diatomaceous earth material is a material originating from the fossilized skeletons of minute, prehistoric aquatic organisms. It is used as a filter aid to assist in the separation of solids from liquids. It is typically processed into powders of various particle size which meet a wide range of industrial filtration requirements.

Filtration is a process by which particles are separated from a fluid by passing the fluid through a permeable material. The permeable material is called the filter medium or membrane. The filter membrane is supported on another permeable material called the filter septum. The filter septum is typically a screen. Ideally, the liquid goes through and solids remain, building a permeable cake on the filter membrane. With large, incompressible particles, this ideal can be approached. In practice, however, finer solids often pass through with only larger solids remaining on the filter membrane. If the retained solids are at all compressible, the liquid flow rate is reduced to an uneconomical level. In the case of the manufacture of recombinant plasmid DNA, a reduced flow rate translates into loss of plasmid DNA given its limited stability (especially in a cell lysate). Diatomaceous earth material functions to approach ideal filtration conditions.

Crude diatomaceous earth material is mined and then processed to serve as a filter aid. It is usually processed by milling, calcining and air classification to give a finished, virtually inert filter aid which is predominantly silica. When deposited on a filter membrane, the diatomaceous earth material forms a rigid but porous filter cake which sieves out the particulate matter in liquid as it passes through the filter.

Filtration using diatomaceous earth material is commonly a two-step operation. First, a thin protective layer of filter aid, called the precoat, is built up on the filter medium by recirculating a filter aid slurry. After precoating, filter aid is added to the liquid to be filtered. As filtering progresses, the filter aid, mixed with the suspended solids from the unfiltered liquid, is deposited on the precoat. Thus, a new filtering surface is continuously formed. The minute filter aid particles provide countless microscopic channels which entrap suspended impurities but allow clear liquid to pass through without clogging.

An efficient, economic filter aid will have rigid, intricately shaped, porous, individual particles; will form a highly permeable, stable, incompressible filter cake; will remove even the finest solids at high rates of flow; and will be chemically inert and essentially insoluble in the liquid being filtered. Diatomaceous earth material meets these requirements due to the wide variety of intricately shaped particles and inert composition.

Filter aid grades are available providing a wide range of particle sizes to meet industrial filtration requirements. Diatomaceous earth material that is the finest will usually give the highest clarity and lowest flow rate. To create this grade, diatomite may be selectively quarried, dried, milled and air-classified. To make coarser, faster flow rate filter aids, diatomite is calcined and air-classified. These are called straight calcined grades. To obtain still larger particles, a flux is added before calcination giving the flux-calcined filter aids. These are the coarsest grades.

In addition to these standard grades of diatomaceous earth material, specialized products may be produced for a wide variety of filtration applications. Acid-washed filter aids are available by acid washing to reduce iron and calcium content for use where exceptional purity is needed. Analytical grade filter aids are obtainable by maximum acid washing for use as an aid in analytical work or where extra exceptional purity is desired.

Selection of the proper filter aid grade is a compromise between high clarity and low flow rate. The best filter aid is the grade that provides the fastest flow rate while maintaining an acceptable degree of clarity, which must be determined and specified by the filter aid user. Selection is empirical and within the skill of workers in the art.

For a given filtration, clarity of filtrate is governed principally by: grade and amount of filter aid for filtration; grade and amount of filter aid for precoat; length of cycle; and filtration rate.

Determination of the degree of clarity obtainable by any one grade of filter aid can be gained by running filtration tests using proper techniques, for example, on a Buchner funnel, and is within the level of skill in the art.

In the normal operation of a filtration system, the filter is first precoated by circulating a mixture of filter aid and liquid through the filter. The precoat acts to prevent the filter membrane from becoming clogged by impurities. The amount of precoat, precoat slurry concentration and precoating rate are selected based on filtration theory and running filtration tests.

After precoating, filtering begins. Care should be taken not to disrupt the precoat. The amount of filter aid that is used is determined on the basis of proper filtration theory and conventional lab tests. The addition of too small an amount is disadvantageous. It results in clogging. This amount is simply inadequate for the filter aid to function properly. Neither is the addition of too large an amount beneficial. It also results in clogging. This amount is in excess for the filter aid to produce the results intended.

Diatomaceous earth materials are distinguishable on the basis of various physical properties. The median particle size can vary from about 10 to about 60 microns. The median cake pore size can fluctuate from about 1 to about 25 microns. The dry density can vary from about 5 to about 20 lbs./cu.ft. Based on a typical chemical analysis, the content of silica can vary from about 85 to about 90% silica. The other constituents of diatomaceous earth material can include $Al_2O_2$, $Fe_2O_3$, $P_2O_5$, $TiO_2$, CaO, MgO, and $Na_2O+K_2O$. These components can be present in variable amounts, for example, $Al_2O_2$ from about 3.3 to about 4.5%, $Fe_2O_3$ from about 1.1 to about 1.5%, $P_2O_5$ from about 0.2 to about 0.3%, TiO2 at about 0.2%, CaO from about 0.5 to about 0.8%, MgO from about 0.6 to about 0.7%, and $Na_2O+K_2O$ from about 1.0 to about 4.2%.

In a preferred embodiment, the diatomaceous earth material is a calcined filter aid. It is flux calcined (as opposed to straight calcined). It is acid washed (to analytical grade quality). The median particle size is about 22.3 microns. The median cake pore size is about 7.0 microns. The dry density is about 10 lbs./cu.ft. It contains about 89.6% $SiO_2$, about 4.0% $Al_2O_2$, about 1.5% $Fe_2O_3$, about 0.2% $P_2O_5$, about 0.2% $TiO_2$, about 0.5% CaO, about 0.6% MgO, and about 3.3% $Na_2O+K_3O$.

We prefer CELITE® HYFLO SUPER CEL® diatomaceous earth filter aid, a course grade, available from Celite Corp., Lompoc, Calif.

Filter aids that are composed of a diatomaceous earth material in combination with other materials are regarded as falling within the scope of the present invention. For example, diatomaceous earth can be combined with a cellulose fiber, as in, e.g., CELITE® Fibra Cel diatomaceous earth filter aid and certain Cuno Zeta Plus filter aids obtainable from Cuno, Meriden, Conn. Cellulose fiber equivalents are envisioned, and other blends are contemplated.

In another embodiment of the invention for reducing RNA concentration in a mixture of biological material, a mixture of biological material having a first concentration of RNA is provided. The mixture is exposed to a diatomaceous earth material to produce a product which, following separation from the diatomaceous earth material by filtration, centrifugation or sedimentation, has a second concentration of RNA, where the second concentration is less than the first concentration. Finally, the product having a reduced RNA concentration is collected.

The invention is useful to purify recombinant plasmid DNA from a RNA component in a mixture of biological material. In this embodiment, one provides a mixture of biological material comprising recombinant plasmid DNA and having a first concentration of RNA. One then filters the mixture through a diatomaceous earth material to produce a filtrate comprising the recombinant plasmid DNA and having a second concentration of RNA, where the second concentration is less than the first concentration. Finally, one collects the filtrate having a reduced RNA component.

This process is useful for the purification of a nucleic acid-based pharmaceutical.

The process of the invention is not limited to circular, supercoiled plasmids (e.g., supercoiled monomers, dimers, concatemers), but applies generally to other supercoiled DNA molecules including chloroplasts, mitochondria, etc., and to different forms (e.g., different replicating forms) of circular DNA molecules, and also to linear DNA molecules, e.g., chromosomal DNA and oligonucleotide DNA.

Neither is the invention limited to plasmids having a particular size or constitution. It has general applicability across plasmids of every kind, regardless of size and constitution. See Examples. We have used the invention to purify, e.g., pBR322- and pUC- based, bicistronic and mono-cistronic, and human- and nonhuman-originating, plasmids alike.

Additionally, this process may be applicable to the separation of different forms of RNA in a mixture of biological material. There is an effort in some laboratories to perform gene therapy with RNA rather than DNA. A purification process that selectively removes host contaminant RNA has tremendous value, when the object of the separation is the recovery of a particular form of RNA.

In this embodiment, one provides a mixture of biological material having a first and second form of soluble RNA. One then filters the mixture through a diatomaceous earth material to produce a filtrate comprising the first form of RNA and a product comprising the second form of RNA that collects in the diatomaceous earth material. Finally, one collects the filtrate. Alternatively, one may elute the second form of RNA from the diatomaceous earth material, given that is the preferred form.

A preferred protocol for purification of recombinant plasmid DNA from a RNA component in a mixture of biological material is presented in Table 2. Here the mixture is a cell lysate. Also, this is a start-to-finish protocol where plasmid DNA is purified to pharmaceutical-grade standards for use as a nucleic acid-based pharmaceutical.

TABLE 2

PROCESS FOR PURIFICATION OF PHARMACEUTICAL-GRADE PLASMID DNA
1. Cell Paste
2. Resuspend Cells in Buffer
3. Lyse Cells in Dilute Base and Detergent
4. Acidify Lysate to Precipitate Host DNA and *E. coli* Proteins
5. Remove Cell Debris and Other Impurities by Centrifugation, Filtration or Sedimentation
6. Clarify Supernatant by Filtration with a Diatomaceous Earth Material
7. Precipitate DNA with PEG-8000 from Clarified Filtrate
8. Collect DNA via Filtration
9. Dissolve DNA in Buffer and Precipitate RNA, Proteins and Lipopolysaccharide Impurities with Ammonium Acetate
10. Separate DNA from Impurities via Filtration
11. Precipitate DNA with Isopropanol
12. Recover Plasmid DNA Pellet in Buffer
13. Size Exclusion Chromatography on Pharmacia S-1000 Removes Remaining Impurities (Higher Molecular Weight Forms of DNA, RNA, Protein and Endotoxin)
14. Analyze Product Fractions, Pool and Ethanol Precipitate
15. Adjust Concentration with Injection Vehicle and Sterile Filter
16. Standard Bulk Plasmid DNA Preparation
17. Final Formulation, Sterile Fill and Finish This process for the purification of pharmaceutical-grade plasmid DNA is elaborated below.

Cell Lysis. The cell paste is resuspended completely in 6 ml per gram wet bacterial weight of cold Solution I (61 mM glucose+25 mMTris buffer pH 8.0+10 mMEDTA at 5° C.) with stirring at room temperature. To this solution 12 ml per gram wet bacterial weight Solution II (0.2N NaOH+1% SDS) is added and mixed end-over-end until homogeneous. This is incubated on wet ice for approximately 10 minutes. To the lysed cell solution, 9 ml per gram wet bacterial weight of cold Solution III (3.0M potassium acetate pH 5.0 at 5° C.) is added, mixed end-over-end until a white flocculent precipitate appears, and incubated on wet ice for approximately 5 minutes.

Filtration. The cell debris is removed from the lysate by filtration, centrifugation or sedimentation. The supernatant is collected and clarified by adding approximately 25 g/l diatomaceous earth material and filtering through a (preferably precoated) filter membrane (Whatman #1, 113 or equivalent) arranged in a table top Buchner funnel. Alternatively, the cell debris is removed from the lysate by direct diatomaceous earth material aided filtration. In this case, approximately 90 g/l diatomaceous earth material is added directly to the lysis solution and mixed by swirling until homogenous. The lysate is then filtered through a (preferably precoated) filter membrane (Whatman #1, 113 or equivalent) arranged in a table top Buchner funnel.

We find that precoating is not required. Precoating is preferred. We precoat by making a slurry of diatomaceous earth material in deionized $H_2O$ and evenly filtering it through the filter membrane arranged in the table top Buchner funnel.

The amount of diatomaceous earth material that is added to the cell lysate is determined empirically as discussed above. At the lower end, 10, 15 or 20 g/l can be added. 25 g/l is preferred. At the higher end, 25–30, 40, 100 or 150 g/l can be used. 90 g/l is preferred. These parameters may be maximized to provide the fastest flow rate (or greatest throughput per dollar's worth of filter aid) while maintaining an acceptable degree of clarity.

The diatomaceous earth material filtration step will be optimized by balancing these elements against the additional factor that the diatomaceous earth material acts to bind RNA. Accordingly, parameters, such as flow rate, clarity, grade and amount of filter aid for filtration, grade and amount of filter aid for precoat, length of cycle, filtration rate, throughput, and permeability, etc., will very much depend on the reduction in the concentration of RNA to be achieved. An approximation of the degree of reduction can be gained by running conventional filtration tests. The amount of RNA in the filtrate can be determined in a number of ways, for example, by routine biochemical analyses. See Example 4.

DNA Precipitation. Polyethylene glycol (PEG, e.g., PEG-8000) is added to the filtrate to 5–15% (w/v), plus NaCl to 0.3–1.5M. The PEG suspension is stirred preferably overnight at 2°–8° C. The DNA precipitate is collected by adding approximately 25 g/l of diatomaceous earth material to the PEG suspension and filtering through a (preferably precoated) filter membrane arranged in a table top Buchner funnel. The DNA precipitate is captured in the cake and recovered by suspending the cake in TE buffer (0.01M Tris-base pH 8.0+0.001M EDTA).

RNA, Protein and Lipopolysaccharide Removal. Ammonium acetate is added to the TE buffer to 2.5M and stirred for approximately 30 minutes at 2°–8° C. The suspension, which still contains diatomaceous earth material, is filtered through a (preferably precoated) filter membrane arranged in a table top Buchner funnel. The DNA filtrate is then optionally clarified by sub-micron filtration.

Final DNA Precipitation. A final DNA precipitation is performed with 0.6 volumes of cold isopropanol for a minimum of 2 hours at −20° C. The precipitated DNA is centrifuged in a Sorvall table top centrifuge for 30 minutes at 2000× g or equivalent. The DNA pellets are resuspended in column buffer prior to gel filtration chromatography.

Gel Filtration Chromatography. A Pharmacia S-1000 tandem size exclusion column, DNA exclusion limit of 20,000 bp, (Pharmacia, Piscataway, N.J.) is poured. The S-1000 matrix is an inert and highly stable matrix that is prepared by covalently cross-linking allyl dextran with N,N'-methylenebisacrylamide. The column is poured in two Pharmacia XK26/100 columns (Pharmacia, Piscataway, N.J.) with a final bed height of 80–85 cm (2.6×80 cm) resulting in a total column volume of approximately 900 ml and a total length of approximately 160 cm. The columns are individually pressure packed in one direction, reversed and connected in series for equilibration and operation. The column is equilibrated in column buffer and run at an appropriate flow rate. Cleared lysate plasmid DNA is filtered through a 0.2 μm syringe filter and loaded onto the column. Column operation and fractionation are automated with a Pharmacia FPLC (Pharmacia, Piscataway, N.J.). Fractions (approximately 0.5–5% of column volume) are collected over the product elution zone and analyzed by 0.8% agarose gel electrophoresis. The exact range of product elution is determined from gel analysis. Appropriate fractions are pooled and precipitated with 2 volumes of cold ethanol. This column purified DNA is stored at −20° C. until needed for preparation of standard bulk plasmid DNA. Following chromatography, the column and FPLC are sanitized with at least one column volume of 0.2M NaOH.

Standard Bulk Plasmid DNA Preparation. The ethanol precipitated, column purified DNA is spun at maximum speed in a Sorvall table top centrifuge for 30 minutes at 4°–10° C. or equivalent. The pellets are air-dried and pooled. The pooled pellets are resuspended in injection vehicle. The DNA is then filtered through a 0.2 μm filter into a pyrogen-free container. Samples are taken for sterility testing, quality control and retention, labeled with a description of the product Lot #, Part #, volume, concentration, and date, and stored frozen in quarantine. This information is entered into inventory control for later final formulation, sterile fill and finish.

ADVANTAGES

In this process, diatomaceous earth material facilitates plasmid DNA purification by adsorbing significant quantities of host cell RNA impurities from the process stream. See Example 4. The extraction of RNA is crucial to the purification of plasmid DNA, because RNA accounts for the majority of the nucleic acid in a crude lysate. Any processing step that reduces the load of the RNA impurity is critical to obtaining purified plasmid DNA.

In the above protocol, diatomaceous earth material further facilitates plasmid DNA purification by allowing a rapid direct filtration of a cell lysate. This point is important because plasmid DNA has only limited stability in a cell lysate. Separation of plasmid DNA from cellular debris and other contaminants captured in the diatomaceous earth material cake is crucial for the production of high yield preparations.

Extraction of RNA using a diatomaceous earth material is especially relevant to the field of nucleic acid-based pharmaceuticals, where a gene, DNA, RNA, antisense or triple helix molecule functions therapeutically in the treatment of a disease. Diatomaceous earth material is a reagent generally recognized as safe by drug regulating bodies such as the FDA. Additionally, it replaces the use of RNase for the removal of RNA, which as an animal derived enzyme is susceptible of being contaminated with infectious agents. Compare Table 1 and 2. Moreover, it eliminates the need to use toxic organic solvents, e.g., phenol, to rid the preparation of RNases. Compare Table 1 and 2. Use of diatomaceous earth material is a scalable unit operation amenable to large scale manufacture. It significantly decreases processing time as compared to standard protocols. These attributes distinguish the diatomaceous earth material process from current state of the art procedures and make it especially well-suited for the manufacture of pharmaceutical-grade DNA.

Particular aspects of the invention may be more readily understood by reference to the following examples, which are intended to exemplify the invention, without limiting its scope to the particular exemplified embodiments.

EXAMPLE 1

PURIFICATION OF pHLA-B7 PLASMID

The pHLA-B7 plasmid, intended for use as a gene therapy pharmaceutical, was purified. A model has been described for the immunotherapy of malignancy using a gene encoding an HLA-B7 antigen. The gene is introduced into tumors in vivo by DNA/liposome transfection for in situ production of antigen. Rubin et al., *Human Gene Therapy* 5:1385 (1994); Hersh et al., *Human Gene Therapy* 5:1371 (1994); Vogelzang et al., *Human Gene Therapy* 5:1357 (1994).

The pHLA-B7 plasmid was about 4900 bp in size. It was a pBR322-based plasmid containing a bacterial origin of replication. It encoded the heavy (human HLA-B7 cDNA) and light (chimpanzee β-2 Microglobulin cDNA) chains of a Class 1 MHC antigen designated HLA-B7. These two proteins were expressed on a bi-cistronic mRNA. Eukaryotic cell expression of this mRNA was dependent on a Rous Sarcoma Virus promoter sequence derived from the 3' Long Terminal Repeat. Expression was also dependent on a transcription termination/polyadenylation signal sequence derived from the bovine growth hormone gene. Expression of the heavy chain was regulated by the 5' cap-dependent protein translation start site. Expression of the light chain was regulated by a Cap Independent Translational Enhancer (CITE) sequence derived from the Encephalomyocarditis Virus. The plasmid also encoded a kanamycin resistance gene derived from Tn903.

In this purification, 500 g of wet cell paste was processed, and 29.1 mg of purified plasmid DNA was recovered.

Cell Lysis

About 500 g of cell paste was resuspended in 3 liters of cold Solution I (61 mM glucose+25 mM Tris buffer pH 8.0+10 mM EDTA at 5° C.) with stirring at room temperature. Next, 6 liters of Solution II (0.2N NaOH+1% SDS) was added and mixed end-over-end until homogeneous. This was incubated in wet ice for 10 minutes. Then, 4.5 liters of cold Solution III (3.0M potassium acetate pH 5.0 at 5° C.) was added, mixed end-over-end until a white flocculent precipitant formed, and incubated in wet ice for 10 minutes.

Filtration

Approximately 1200 grams of Celite® diatomaceous earth was added to the lysate and mixed by swirling until homogeneous. A table top Buchner funnel was assembled using Whatman #113 filter paper. The filter paper was pre-coated with Celite® diatomaceous earth in deionized $H_2O$. The lysate was then poured through the filter paper in the filter assembly to permit a CELITE® cake to build up on the filter paper. The total time to filter 13.5 liters was 15 minutes. The total filtrate recovered was 12 liters.

DNA Precipitation

PEG-8000 was added to the filtrate to 10% (w/v), plus NaCl to 0.58 g per gram of original cell mass. The PEG suspension was stirred overnight at approximately 4° C. The DNA precipitate was collected as follows. About 325 grams of Celite® diatomaceous earth was added to the PEG suspension and mixed by swirling until homogeneous. A table top Buchner funnel was assembled using Whatman #113 filter paper. The filter paper was pre-coated with Celite® diatomaceous earth in deionized $H_2O$. The PEG suspension was then poured through the filter paper in the filter assembly to permit a CELITE® cake to build up on the filter paper. The cake was aspirated dry. The DNA precipitate was captured in the CELITE® cake and recovered by suspending the cake in 1 liter of TE buffer (0.01M Tris-base pH 8.0+0.001M EDTA). The total volume came to 1700 ml.

RNA, Protein and Lipopolysaccharide Removal.

Ammonium acetate was added to the TE buffer to 2.5M for 1800 ml and stirred for about 1 hour at approximately 4° C. A table top Buchner funnel was assembled using Whatman #113 filter paper. The filter paper was pre-coated with Celite® diatomaceous earth in deionized $H_2O$. The ammonium acetate suspension, which still contained diatomaceous earth, was then poured through the filter paper in the filter assembly to permit a CELITE® cake to build up on the filter paper. The cake was aspirated dry. The DNA filtrate, coming to 1500 ml, was then clarified by sub-micron filtration through a 0.8 μm bottle top filter.

Reduction of Volume.

Next, the filtrate was concentrated using a Millipore PTGC (nominal molecular weight limit 10,000) Prep/Scale Tangential Flow Filter (Millipore, Bedford, Mass.). The initial volume of 1500 ml was reduced to 620 ml in approximately 90 min. During the process the filtrate was kept on ice.

Final DNA Precipitation.

A final DNA precipitation was performed with 0.6 volumes (375 ml) of cold 2-propanol for a minimum of 2 hours at −20° C. The precipitated DNA was centrifuged in a Sorvall table top centrifuge for 30 minutes at 2000× g. The DNA pellets were resuspended in 24 ml of physiological saline prior to gel filtration chromatography.

Gel Filtration Chromatography.

A Pharmacia S-1000 tandem size exclusion column, DNA exclusion limit of 20,000 bp, (Pharmacia, Piscataway, N.J.) was poured in two Pharmacia XK26/100 columns (Pharmacia, Piscataway, N.J.) with a final bed height of 80–85 cm (2.6×80 cm) resulting in a total column volume of approximately 900 ml and a total length of approximately 160 cm. The columns were individually pressure packed in one direction, reversed and connected in series for equilibration and operation. The column was equilibrated in physiological saline and run at a flow rate of approximately 0.6 ml/min. Cleared lysate plasmid DNA was filtered through a 0.2 μm syringe filter and loaded onto the column. Column operation and fractionation were automated with a Pharmacia FPLC (Pharmacia, Piscataway, N.J.). Fractions (approximately 0.5–5% of column volume) were collected over the product elution zone and analyzed by 0.8% agarose gel electrophoresis. The exact range of product elution was determined from gel analysis. Appropriate fractions were pooled and precipitated with 2 volumes of cold ethanol. This column purified DNA was stored at −20° C. until needed. Following chromatography, the column and FPLC were sanitized with at least one column volume of 0.2M NaOH.

EXAMPLE 2

PHARMACEUTICAL-GRADE PURIFIED pHLA-B7 PLASMID

Plasmid DNA of Example 1 was purified to pharmaceutical-grade standards as determined by the criteria given in Table 3 below.

TABLE 3

| QUALITY CONTROL CRITERIA | | |
|---|---|---|
| TEST | SPECIFICATION | METHOD |
| Size Identity | Approximates: 4900 bp | Agarose Gel Electrophoresis |
| Restriction Sites | Approximates predicted: XhoI/XbaI - 3500 & 1400 bp, BglII/XhoI - 2100, 1700 & 1000 bp | Agarose Gel Electrophoresis |
| Circular Plasmid DNA | > 95% of visualized nucleic acid | Agarose Gel Electrophoresis |
| A260/A280 Ratio | 1.75 to 2.00 | UV Absorbance |
| E coli DNA | < 0.01 μg/μg plasmid DNA | Southern Slot Blot |
| RNA | Non-visualized on gel | Agarose Gel Electrophoresis |
| Protein | Undetectable | BCA Colorimetric Assay |
| Pyrogenicity | Not pyrogenic at 5 μg/Kg rabbit body weight | Rabbit Pyrogen Assay |
| Endotoxin | < 0.1 EU/μg plasmid DNA | Limulus Amebocyte Lysate (LAL) Assay |
| Sterility | No growth through 14 days | Fluid Thioglycollate Assay |
| Potency | 50–200% of reference | In Vitro Transfection/ Fluorescence |
| General Safety Test | Passes | per 21 C.F.R. 610.11 |

EXAMPLE 3

POTENCY OF PURIFIED pHLA-B7 PLASMID

Potency of pHLA-B7 plasmid purified according to Example 1 was determined by HLA-B7 gene expression in HALL cells (a human melanoma cell line) following lipid-mediated in vitro transfection using DMRIE/DOPE.

From 200,00 to 400,000 HALL cells were seeded per well into a 6-well plate the day before transfection. Cells were a >75% confluent monolayer prior to transfection. The cells were transfected with 5 μg plasmid DNA in the presence of 5 μg DMRIE (synthesized in house) and 5 μg DOPE (synthesized by Avanti Polar Lipids, Inc., Alabaster, Ala.). The cells were incubated at 37° C., 5% $CO_2$ throughout. A reduced serum medium, e.g., Opti-MEM (GIBCO BRL Life Technologies, Baltimore, Md.), supplemented with fetal calf serum, was added to the cells 1–4 hours and 24 hours post-transfection. Cells were harvested 48 hours post-transfection.

HLA-B7 expression on the cell surface was measured by labelling with anti-HLA-B7 mouse antibody, followed by a fluorescent secondary antibody (anti-mouse IgG monoclonal antibody R-phycoerrythin conjugate). Immunofluorescent staining of the cells was analyzed by flow cytometry. A two-fold increase in mean fluorescence intensity was observed for transfected cells in contrast to negative controls (non-transfected cells or cells transfected with an irrelevant gene). Potency was 50–200% relative to a reference lot.

EXAMPLE 4

REDUCING RNA CONCENTRATION USING CELITE® DIATOMACEOUS EARTH

The plasmid purification steps of Example 1 were evaluated by agarose gel electrophoresis. Following cell lysis and CELITE® diatomaceous earth aided filtration, and after DNA precipitation by PEG and Celite® aided clarification, we performed the following analysis. The cake was resuspended in TE buffer and filtered through a CELITE® diatomaceous earth precoated Whatman #113 filter arranged in a table top Buchner funnel. An aliquot of filtrate was electrophoresed on a 0.8% agarose gel. Additionally, an aliquot of a buffer wash of the CELITE® cake was coelectrophoresed on the same gel.

The ethidium bromide stained gel was analyzed. Product plasmid DNA was present as supercoiled monomers, dimers and concatemers in the Celite® filtrate. The buffer wash of the CELITE® cake was found to contain contaminant host RNA. This was a surprising result, because RNA was not expected to collect in the Celite® diatomaceous earth cake.

Semi-quantitative analysis revealed that in any one step such as this representative one, the concentration of RNA was reduced by as much as about 85%.

EXAMPLE 5

PURIFICATION OF pCMVIL2BGH PLASMID

The pCMVIL2BGH plasmid, intended for use as a gene therapy pharmaceutical, was purified. An approach has been developed that relies on the direct intralesional administration of recombinant genes into established tumors in vivo. The genes genetically modify the tumors, as they grow in situ, to produce and secrete local amounts of Interleukin-2 (IL-2). Interleukin-2 is intended to destroy the tumor.

The pCMVIL2BGH plasmid was about 4900 bp in size. It was a pUC-based plasmid containing a bacterial origin of replication. It encoded an IL-2 fusion protein. The protein was constructed by cloning a portion encoding a short segment of the 5' untranslated region and the first six amino acids of the leader peptide of the rat insulin II gene 5' of the human IL-2 coding sequence minus the first two amino acids of its leader peptide. This fusion protein was placed under the eukaryotic transcriptional control of the cytomegalovirus (CMV) immediate early 1 promoter/enhancer sequence. This sequence facilitated expression of a composite mRNA containing a 5' untranslated sequence from the CMV immediate early 1 gene, including the 800+ bp intron, the IL-2 fusion protein coding sequence, and a 3' untranslated sequence derived from the bovine growth hormone gene having transcription termination/polyadenylation signal sequence. The plasmid also encoded a kanamycin resistance gene derived from Tn903.

In this purification, 490 g of wet cell paste was processed, and 10.2 mg of purified plasmid DNA was recovered.

Cell Lysis. The cell paste was resuspended in 6 ml per gram wet bacterial weight of cold Solution I (61 mM glucose +25 mM Tris buffer pH 8.0+10 mM EDTA at 5° C.) with stirring at room temperature. Next, 12 ml per gram wet bacterial weight Solution II (0.2N NaOH+1% SDS) was added and mixed end-over-end until homogeneous. This was incubated in wet ice for 10 minutes. Then, 9 ml per gram wet bacterial weight of cold Solution III (3.0M potassium acetate pH 5.0 at 5° C.) was added, mixed end-over-end until a white flocculent precipitant formed, and incubated in wet ice for 5 minutes.

Filtration. The cell debris was removed from the lysate by centrifugation. The supernatant was collected and clarified by adding approximately 25 g/l Celite® diatomaceous earth and filtering through a table top Buchner funnel. Alternatively, approximately 90 g/l Celite® diatomaceous earth could be added directly to the lysis solution and mixed by swirling until homogeneous. The lysate could then be filtered through a table top Buchner funnel.

DNA Precipitation. PEG-8000 was added to the filtrate to 10% (w/v), plus NaCl to 0.58 g per gram of original cell mass. The PEG suspension was stirred overnight at approximately 4° C. The DNA precipitate was collected by adding about 25 g/l of Celite® diatomaceous earth to the PEG suspension and filtering through a table top Buchner funnel. The DNA precipitate was captured in the CELITE® cake and recovered by suspending the cake in TE buffer (0.01M Tris-base pH 8.0+0.001M EDTA).

RNA, Protein and Lipopolysaccharide Removal. Ammonium acetate was added to the TE buffer to 2.5M and stirred for about 30 minutes at approximately 4° C. The suspension, which still contained Celite® diatomaceous earth, was filtered through a table top Buchner funnel. The DNA filtrate was then clarified by sub-micron filtration.

Final DNA Precipitation. A final DNA precipitation was performed with 0.6 volumes of cold 2-propanol for a minimum of 2 hours at −20° C. The precipitated DNA was centrifuged in a Sorvall table top centrifuge for 30 minutes at 2000× g. The DNA pellets were resuspended in physiological saline prior to gel filtration chromatography.

Gel Filtration Chromatography. A Pharmacia S-1000 tandem size exclusion column, DNA exclusion limit of 20,000 bp, (Pharmacia, Piscataway, N.J.) was poured in two Pharmacia XK26/100 columns (Pharmacia, Piscataway, N.J.) with a final bed height of 80–85 cm (2.6×80 cm) resulting in a total column volume of approximately 900 ml and a total length of approximately 160 cm. The columns were individually pressure packed in one direction, reversed and connected in series for equilibration and operation. The column was equilibrated in physiological saline and run at a flow rate of approximately 0.75 ml/min. Cleared lysate plasmid DNA was filtered through a 0.2 μm syringe filter and loaded onto the column. Column operation and fractionation were automated with a Pharmacia FPLC (Pharmacia, Piscataway, N.J.). Fractions (approximately 0.5–5% of column volume) were collected over the product elution zone and analyzed by 0.8% agarose gel electrophoresis. The exact range of product elution was determined from gel analysis. Appropriate fractions were pooled and precipitated with 2 volumes of cold ethanol. This column purified DNA was stored at −20° C. until needed. Following chromatography, the column and FPLC were sanitized with at least one column volume of 0.2M NaOH.

EXAMPLE 6

PHARMACEUTICAL-GRADE PURIFIED pCMVIL2BGH PLASMID

Plasmid DNA of Example 6 was purified to pharmaceutical-grade standards as determined by the criteria given in Table 4 below.

TABLE 4

QUALITY CONTROL CRITERIA

| TEST | SPECIFICATION | METHOD |
|---|---|---|
| Size Identity | Approximates 4900 bp | Agarose Gel Electrophoresis |
| Restriction Sites | Approximates predicted: EcoRI - 3000 & 1900 bp, NcoI - 3700 & 1200 bp | Agarose Gel Electrophoresis |
| Circular Plasmid DNA | > 95% of visualized nucleic acid | Agarose Gel Electrophoresis |
| A260/A280 Ratio | 1.75 to 2.00 | UV Absorbance |
| E coli DNA | < 0.01 µg/µg plasmid DNA | Southern Slot Blot |
| RNA | Non-visualized on gel | Agarose Gel Electrophoresis |
| Protein | < 0.016 µg/µg plasmed DNA | Protein Slot Blot |
| Residual Ethanol | < 500 ppm | Gas Chromatography |
| Pyrogenicity | Not pyrogenic at 5 µg/Kg rabbit body weight | Rabbit Pyrogen Assay |
| Endotoxin | < 0.1 EU/µg plasmid DNA | Limulus Amebocyte Lysate (LAL) Assay |
| Sterility | No growth through 14 days | USP Direct Transfer |
| Potency | 50–200% of reference | In Vitro Tranfection/ ELISA |
| General Safety Test | Passes | USP General Safety Test |

EXAMPLE 7

POTENCY OF PURIFIED pCMVIL2BGH PLASMID

Potency of pCMVIL2BGH plasmid purified according to Example 5 was determined by IL-2 gene expression in B16F0 cells (a mouse melanoma cell line) following lipid-mediated in vitro transfection using DMRIE/DOPE.

From 200,00 to 400,000 B16F0 cells were seeded per well into a 6-well plate the day before transfection. Cells were a >75% confluent monolayer prior to transfection. The cells were transfected with 2.5 µg plasmid DNA in the presence of 0.5 µg DMRIE (synthesized in house) and 0.5 µg DOPE (synthesized by Avanti Polar Lipids, Inc., Alabaster, Ala.). The cells were incubated at 37° C., 5% $CO_2$ throughout. A reduced serum medium, e.g., Opti-MEM (GIBCO BRL Life Technologies, Baltimore, Md.), supplemented with fetal calf serum, was added to the cells 1–4 hours and 24 hours post-transfection. Cell supernatant was harvested 80 hours post-transfection.

IL-2 expression in the cell supernatant was measured by an enzyme amplified sensitivity immunoassay (Medgenix ELISA, Medgenix Diagnostics, Fleurus, Belgium). Potency was 50–200% relative to a reference lot.

EXAMPLE 8

PURIFICATION OF pCMVBGH PLASMID

The pCMVBGH plasmid was purified. This plasmid was about 4300 bp in size. It contained all the elements found in pCMVIL2BGH, excluding the human IL-2 coding sequence.

Using the purification steps described in Example 6 above, 503 g of wet cell paste was processed, and 14.1 mg of purified plasmid DNA was recovered.

We provide a process for reducing the RNA concentration in a mixture of biological material by using a diatomaceous earth material. This is a new use for a diatomaceous earth material. We appreciate that the diatomaceous earth material retains as much as about 85% of the available RNA.

While particular embodiments of the invention have been described in detail, it will be apparent to those skilled in the art that these embodiments are exemplary rather than limiting, and the true scope of the invention is that defined within the attached claims.

What is claimed is:

1. A process for reducing RNA concentration in a mixed solution of RNA and DNA comprising the steps of:
    (a) providing RNA and DNA in a solution, said solution having a first concentration of RNA;
    (b) filtering said solution through an effective amount of diatomaceous earth, wherein the RNA will bind to diatomaceous earth more strongly than will DNA, to produce a filtrate having a second concentration of RNA, wherein the second concentration is less than the first concentration; and
    (c) collecting said filtrate having a reduced RNA concentration, wherein said process is conducted in the absence of a toxic organic solvent.

2. The process of claim 1, wherein the RNA concentration is reduced by at least about 10%.

3. The process of claim 1, wherein the RNA concentration is reduced by at least about 25%.

4. The process of claim 1, wherein the RNA concentration is reduced by at least about 50%.

5. The process of claim 1, wherein the RNA concentration is reduced by at least about 85%.

6. The process of claim 1, wherein said mixture is a cell lysate.

7. The process of claim 1, wherein said diatomaceous earth material is composed of about 90% $SiO_2$.

8. The process of claim 1, wherein said diatomaceous earth material is calcined.

9. The process of claim 8, wherein said calcined diatomaceous earth material is flux calcined.

10. The process of claim 9, wherein said flux calcined diatomaceous earth material is acid washed.

11. The process of claim 1, wherein said diatomaceous earth material has a dry density of about 10 lbs/cu.ft.

12. The process of claim 1, wherein said diatomaceous earth material has a median particle size of about 22.3 microns.

13. The process of claim 1, wherein said diatomaceous earth material has a median cake pore size of about 7 microns.

14. The process of claim 1, wherein said diatomaceous earth is composed of about 89.6% $SiO_2$, about 4.0% $Al_2O_2$, about 1.5% $Fe_2O_3$, about 0.2% $P_2O_5$, about 0.2% $TiO_2$, about 0.5% CaO, about 0.6% MgO, and about 3.3% of an oxide selected from the group consisting of $Na_2O$ and $K_2O$, or a combination thereof.

15. A process for reducing RNA concentration a mixed solution of RNA and DNA comprising the steps, of:
    (a) providing RNA and DNA in a solution, said solution having a first concentration of RNA;
    (b) contacting said solution with an effective amount of diatomaceous earth, wherein the RNA will bind to diatomaceous earth more strongly than will DNA, to produce a liquid product which, following separation from said diatomaceous earth by filtration, centrifugation or sedimentation, has a second concentration of RNA, wherein the second concentration is less than the first; and (c) collecting said product having a reduced RNA concentration, wherein said process is conducted in the absence of a toxic organic solvent.

16. A process for purifying recombinant plasmid DNA from a RNA component in a mixture of RNA and DNA, comprising the steps of:

(a) providing a solution comprising recombinant plasmid DNA and RNA, said solution having a first concentration of RNA;

(b) filtering said solution through an effective amount of diatomaceous earth, wherein the RNA will bind to diatomaceous earth more strongly than will DNA, to produce a filtrate comprising said recombinant plasmid DNA and having a second concentration of RNA, wherein the second concentration is less than the first concentration; and (c) collecting said filtrate having a reduced RNA component, wherein said process is conducted in the absence of a toxic organic solvent.

17. The process of claim 16, wherein said recombinant plasmid DNA is a component of a pharmaceutical preparation.

18. A process for separating different forms of soluble RNA in a solution of RNA, comprising the steps of:

(a) providing a solution of RNA, said solution having a first and a second form of soluble RNA; and (b) filtering said solution through an effective amount of diatomaceous earth, wherein some forms of RNA will bind to diatomaceous earth more strongly than will other forms of RNA, to produce a filtrate comprising said first form of soluble RNA and a product comprising said second form of soluble RNA that collects in said diatomaceous earth, wherein said process is conducted in the absence of a toxic organic solvent.

19. The process of claim 18, wherein one of said forms of RNA is a component of a pharmaceutical preparation.

20. A process for purifying recombinant plasmid DNA from a RNA component in a mixed solution of RNA and DNA, comprising the steps of:

(a) providing a solution comprising recombinant plasmid DNA and RNA, said solution having a first concentration of RNA;

(b) adding an effective amount of diatomaceous earth, wherein the RNA will bind to diatomaceous earth more strongly than will DNA, to said solution;

(c) mixing the result of step (b) to form a suspension;

(d) pouring said suspension through a diatomaceous earth precoated filter membrane to allow a diatomaceous earth cake to collect on said filter membrane and to form a filtrate comprising said recombinant plasmid DNA and having a second concentration of RNA, wherein the second concentration is less than the first concentration; and (e) collecting said filtrate having a reduced RNA component, wherein said process is conducted in the absence of a toxic organic solvent.

* * * * *